United States Patent [19]

Armbruster et al.

[11] 3,957,587

[45] May 18, 1976

[54] PRODUCTION OF XYLOSE (DEXTROSE) ISOMERASE ENZYME PREPARATIONS

[75] Inventors: Frederick C. Armbruster, La Grange; Robert E. Heady, Park Forest; Robert P. Cory, La Grange, all of Ill.

[73] Assignee: CPC International Inc., Englewood Cliffs, N.J.

[22] Filed: June 23, 1975

[21] Appl. No.: 589,115

Related U.S. Application Data

[60] Continuation of Ser. No. 417,989, Nov. 21, 1973, abandoned, which is a division of Ser. No. 181,639, Sept. 17, 1971, Pat. No. 3,813,318.

[52] U.S. Cl. ............................ 195/66 R; 195/31 F; 195/62; 195/79; 195/112
[51] Int. Cl.² ................. C12D 13/00; C12D 13/10; C12K 1/02
[58] Field of Search .................. 195/31 F, 66 R, 65, 195/62, 31 R, 112, 79, 102

[56] References Cited
UNITED STATES PATENTS

| | | | |
|---|---|---|---|
| 3,616,221 | 10/1971 | Takasaki et al. | 195/31 F |
| 3,622,463 | 11/1971 | Iizuka et al. | 195/31 F |
| 3,623,953 | 11/1971 | Cotter et al. | 195/31 F |
| 3,625,828 | 12/1971 | Brownwell | 195/66 R |
| 3,645,848 | 2/1972 | Lee et al. | 195/31 F |
| 3,654,080 | 4/1972 | Bengtson et al. | 195/31 F |
| 3,689,362 | 9/1972 | Takasaki et al. | 195/31 R |

FOREIGN PATENTS OR APPLICATIONS

| | | | |
|---|---|---|---|
| 417,428 | 11/1966 | Japan | 195/31 F |

OTHER PUBLICATIONS

Lamanna et al., *Basic Bacteriology*, 3rd ed., The Williams and Wilkon Co., Baltimore, (1965), pp. 723–727.

*Primary Examiner*—Alvin E. Tanenholtz
*Assistant Examiner*—Thomas G. Wiseman
*Attorney, Agent, or Firm*—Albert P. Halluin

[57] ABSTRACT

Process for the production of xylose (dextrose) isomerase by means of a mutant strain of Streptomyces that proliferates in a culture medium that may be free of xylose. The xylose (dextrose) isomerase enzyme is therefore constitutive rather than induced.

15 Claims, No Drawings

PRODUCTION OF XYLOSE (DEXTROSE) ISOMERASE ENZYME PREPARATIONS

CROSS-REFERENCE TO RELATED APPLICATION

This application is a continuation of U.S. patent application Ser. No. 417,989, filed Nov. 21, 1973, now abandoned which in turn is a division of U.S. patent application Ser. No. 181,639, filed Sept. 17, 1971, now U.S. Pat. No. 3,813,318, granted May 28, 1974.

Field of the Invention

This invention relates generally to enzymatic isomerization. More particularly, the invention relates to improvements in the production of enzyme preparations that are useful for the isomerization of dextrose to levulose, and to their use for such isomerizations. The invention also relates to novel isomerase enzyme preparations.

BACKGROUND

The production of corn syrup and corn syrup solids, by the hydrolysis of starch, has progressed in the direction of ever sweeter products. The acid hydrolyzates that were the initial commercial products have gradually given way to generally superior products produced by the use of sacchrifying enzymes. The art has advanced to the point were enzyme hydrolyzates can be routinely produced on a commercial scale at D.E. values in excess of 95.

However, the industry is interested in even greater sweetness, and research has been conducted for years into techniques for isomerizing starch hydrolyzates to increase the content of levulose. Important initial work in the field was conducted by Cantor and Hobbs, as reported in U.S. Pat. No. 2,354,664, granted Aug. 11, 1944. Cantor and Hobbs utilized alkali catalysis to effect isomerization.

Alkali isomerization is limited in the degree to which the isomerization can be carried out efficiently and with the formation of commercially acceptable products. Consequently, there was a widespread search for many years for an enzyme that would effect the isomerization. This search culminated in the discovery that xylose isomerase, which catalyzes the interconversion of D-xylose and D-xylulose, did convert D-glucose (dextrose) to D-fructose (levulose), as described by Marshall and Kooi in *Science*, Apr. 5, 1957, Vol. 125, No. 3249, pages 648–649, and in the pioneer patent in the field, U.S. 2,950,228, to Richard O. Marshall, on Aug. 23, 1960. Since that time, there has been a great amount of research activity in connection with enzymatic isomerization.

The use of a microorganism of the Actinomycetales order, for the production of an isomerizing enzyme, was reported by Sato and Tsumura in their paper, "A Study on Isomerization of Dextrose by a Streptomyces Strain", at the Annual Meeting of the Agricultural Chemical Society of Japan held at Sapporo in July, 1964. A great deal of subsequent work, relating to the use of microorganisms of the Streptomyces genus for isomerase enzyme production, has been conducted at the Fermentation Research Institute of Japan, as reported by Dr. Y. Takasaki and his associates. Some of this work has been summarized in the publication, *Fermentation Advances*, Academic Press, New York, 1969, in the article by Dr. Takasaki et al. beginning at page 561.

The work of Sato and Tsumura led to the use of Streptomyces microorganisms for the production of isomerizing enzymes by the use of a nutrient medium containing xylose. Unfortunately, if xylose is required for enzyme production, there are limitations on the nature and cost of the medium that is required. Dr. Takasaki and his associates identified certain strains of Streptomyces that secreted xylanase, and that therefore could be cultured in nutrient media containing xylan, which is much less expensive than xylose. Unfortunately, the economics and other limitations on the nature and cost of the culture media required even for these microorganisms impose severe limitations on the process. Moreover, all known strains have been thought to require the presence of cobalt in the culture medium for practical enzyme production, and this created a disposal problem.

OBJECTS OF THE INVENTION

One object of the present invention is to provide new and improved practical techniques for the production of isomerizing enzyme preparations that do not require the use of xylose to induce the production of the enzyme.

A closely related object of the invention is to provide practical techniques for the production of isomerizing enzyme that do not require the use of cobalt in the culture medium.

A more general object of the invention is to provide practical processes for the production of isomerizing enzyme for converting starch hydrolyzates or dextrose solutions to levulose-bearing products, that are more attractive for commercial exploitation than prior art processes.

A related general object of the invention is to provide an improved practical process for the production of levulose-bearing products.

Other objects of the invention will be apparent hereinafter from the specification and from the recitals of the appended claims.

DEFINITIONS

Because of the plethora of terms that are in common use in the art, a few definitions are made to simplify the present application and permit it to be more concise.

D.E. The term "D.E." is an abbreviation for "dextrose equivalent", and these terms are used interchangeably to refer to the reducing sugar content of a material calculated as dextrose and expressed as percent of total solids.

Starch hydrolyzate. The term "starch hydrolyzate" is used in a general way to refer to a syrup or dry product that is made by the hydrolysis of starch. Such a product may be made by acid or enzymatic hydrolysis, or by a combination of acid and enzymatic hydrolysis. A preferred type of starch hydrolyzate for use for isomerization in accordance with the present invention is produced by acid or enzyme thinning to a D.E. of 10 or less, followed by enzymatic saccharification to a D.E. above 95, and preferably above 97.5.

Glucose and dextrose. Medium D.E. starch hydrolyzates are commonly referred to in the art as "glucose", whether the starch hydrolyzate is in the form of a syrup or in the form of solids. The term "dextrose" is commonly reserved for the refined crystalline monosaccharide that is recovered from a high D.E. starch hydrolyzate, or for D-glucose as a constituent of starch hydrolyzates. As used hereafter, the term dextrose will be used to embrace this monosaccharide in any form, in solution or dry, as a constituent of a starch hydrolyzate syrup, syrup solids, or in refined crystalline form.

Fructose and levulose. The terms "fructose" and "levulose" are generally employed interchangeably in the art to refer to the isomer of dextrose that is sweeter than dextrose. This isomer is found in honey and in invert sugar, along with dextrose, and it is valuable because of its sweetness. The term levulose will be used to refer to this monosaccharide.

The enzyme. The enzyme that isomerizes dextrose to levulose has been referred to in the art by several names. It is referred to in the Marshall U.S. Pat. No. 2,950,228, as xylose isomerase, because it isomerizes xylose to xylulose. This activity is in addition to its ability to isomerize dextrose to levulose. It has also been referred to in the art as dextrose isomerase and glucose isomerase. The term "xylose isomerase" will be used herein for reasons to be described presently, under the heading, "Characterization of the Enzyme."

Enzyme preparation. The term "enzyme preparation" is used to refer to any composition of matter that exhibits the desired xylose isomerase enzymatic activity. The term is used to refer, for example, to live whole cells, dried cells, cell extracts, and refined and concentrated preparations derived from the cells. Enzyme preparations may be either in dry or liquid form.

Units. In this application, all parts and percentages are by weight, and on an as is basis, unless expressly stated to be otherwise.

Isomerase Unit. One isomerase unit is defined as the amount of enzyme activity that is required to produce one micromole of levulose per minute under the isomerization conditions described hereafter under the heading, "Assay of Isomerase Activity."

Streptomyces. This term refers to a genus of microorganisms of the order of Actinomycetales. These microorganisms are serial myceliumproducing actinomycetes. The genus is well recognized. Some of its important distinguishing characteristics are described, for example, in the text, "The Actinomycetes", by Selman A. Waksman, The Ronald Press Company, New York, 1967, page 135 et seq.

BRIEF SUMMARY OF THE INVENTION

We have now discovered that it is possible to produce xylose isomerase enzyme preparations on a practical basis by cultivating in a nutrient medium a microorganism of the genus Streptomyces that is characterized by its capacity to form an appreciable quantity of xylose isomerase when cultivated in a nutrient medium that is free from xylose and xylose-supplying material and that is essentially free of cobalt.

The preferred microorganisms are mutant strains of *Streptomyces olivochromogenes*, especially *S. olivochromogenes* ATCC Nos. 21,713, 21,714, 21,715, and their equivalents. These microorganisms have the requisite functional characteristics, that is, they do form appreciable quantities of xylose isomerase when cultivated in nutrient media that are free of xylose and xylose-supplying material and that are free of added cobalt. While these specific microorganisms are preferred, it is believed that any microorganism of the genus Streptomyces can be mutated to secure a strain having the desired characteristics.

While it is possible, in accordance with the invention, to produce suitable enzyme preparations on a practical scale by cultivation of the selected microorganism in a nutrient medium that is free from xylose and xylose-supplying materials and that is also essentially free of cobalt, even better and more economical results are generally obtained when xylose, cobalt, or both, are present in the nutrient medium in which the preferred microorganisms are cultivated.

DETAILED DESCRIPTION OF THE INVENTION

Production of Mutant Strains

A parent strain, S, *olivochromogenes* ATCC 21,114, was selected for mutation because it was known to be a good source of xylose isomerase.

This microorganism was exposed in the spore state to a dose of ultraviolet light sufficient to kill 97% of the exposed microorganisms. The irradiated spores were plated out, and each colony was tested for enzyme activity. Since the medium on which the colonies were grown contained no xylose to induce the formation of isomerase enzyme, only that colony that had the desired characteristics showed a positive enzyme reaction. This colony was isolated and was extensively tested, to demonstrate that the new, mutant strain did indeed produce appreciable quantities of xylose isomerase without the need for xylose in the nutrient medium as an inducing agent.

In greater detail, the steps involved in this procedure were as follows. *S. olivochromogenes* ATCC 21,114 was grown on Difco starch agar, made to 2.0% agar with added agar, until the culture had sporulated abundantly. These spores were then harvested and suspended in 20 ml. of a 0.1% solution of the surfactant, Tween 80 (the trademark of Atlas Powder Co. for a polyoxyalkylene derivative of sorbitan monooleate). Then 0.1% of a dispersing agent, Marasperse C (the trademark of Marathon Paper Mills Co. for a lignin-sulfonic acid dispersing agent) was added, and the suspension was sonicated for two bursts of 15 seconds each, to break up chains and clumps of the spores. The resulting spore suspension was examined and was found to be relatively free of spore chains.

This spore suspension was exposed in a shallow dish, with stirring, to ultraviolet light from a Westinghouse Sterilamp (782H-10) at a distance of four inches for about eight minutes. This exposure produced a 97% kill of the spores. The suspension was then diluted, and at the proper dilution to give about 100 colonies per plate, was streaked out in Petri dishes containing the following medium:

Table 1

| Agar Medium | |
| --- | --- |
| 15 D.E. Corn syrup solids | 1.0% |
| Difco Yeast extract | 0.05% |
| Difco BactoPeptone | 0.05% |
| Difco BactoTryptone | 0.05% |
| Agar | 1.5% |
| pH to 7.5 with NaOH | |

About 40 to 80 colonies per plate did grow and were subsequently isolated. These isolates were screened for the ability to isomerize xylose after being grown on a medium that did not contain xylose or any material supplying xylose.

ISOLATION OF AND FERMENTATION WITH THE MUTANT

One isolate was found that produced isomerase activity when grown in the absence of xylose. The isomerase activity produced was 0.155 units/ml. After a second transfer, the activity was increased to 0.6 units/ml.

The culture was then carried through several more transfers and then was plated out for reisolation. Eleven colonies were selected, grown up on slants, and then grown up through two seed stages. The eleven second seed stages were used to inoculate two culture media, identified below respectively as Medium A and Medium B. In addition, for comparative purposes, a seed grown from the parent culture, *S. olivochromogenes* ATCC 21,114, was also used to inoculate the same two culture media.

The procedure employed and observations made are described in detail below.

For the two seed stages, the medium employed had the composition set forth in Table 2.

Table 2

| First and Second Seed Medium | |
|---|---|
| 15 D.E. Corn syrup solids | 1.0% |
| Corn steep liquor (55% solids) | 3.6% |
| $MgSO_4 \cdot 7H_2O$ | 0.05% |
| $CoCl_2 \cdot 6H_2O$ | 0.024% |
| pH to 7.0 with NaOH, with 1 drop of an antifoaming agent per flask. | |

The first stage seed was carried out for two days, with 100 ml. of the seed medium in each of the required number of 500 ml. Erlenmeyer flasks, utilizing a reciprocating shaker at 28°C. Spores from each of the respective slants were used to inoculate each of these flasks.

The second seed stage was carried out for one day, with 200 ml. of the seed medium in each of the necessary 1-liter Hinton flasks, using a Gump rotary shaker at 28°C. Ten-ml. portions of the first seed were used to inoculate each of the second seed flasks, respectively.

Five-ml. portions of material from the second seed stages were then used to inoculate culture media having the following compositions respectively:

Table 3

| Culture Media A and B | |
|---|---|
| Medium A | |
| 15 D.E. corn syrup solids | 2.0% |
| Corn steep liquor (55% solids) | 3.6% |
| $NH_4NO_3$ | 0.2% |
| Glycine | 0.3% |
| $MgSO_4 \cdot 7H_2O$ | 0.05% |
| $CoCl_2 \cdot 6H_2O$ | 0.024% |
| pH to 7.0 with NaOH | |
| Medium B | |
| Xylose | 2.2% |
| 15 D.E. corn syrup solids | 1.2% |
| Corn steep liquor (55% solids) | 3.6% |
| $NH_4NO_3$ | 0.2% |
| Glycine | 0.3% |
| $CoCl_2 \cdot 6H_2O$ | 0.024% |
| $MgSO_4 \cdot 7H_2O$ | 0.05% |
| pH to 7.0 with NaOH | |

For the fermentation, 100 ml. of the appropriate respective culture medium was placed in each of the necessary 1-liter Hinton flasks. One drop of antifoaming material was added to each flask and the flasks were sterilized, then cooled. After inoculation, the flasks were then placed on a Gump rotary shaker and maintained at 28°C for 2 days.

HARVESTING OF THE ENZYME PREPARATION

After fermentation, the contents of each flask were centrifuged at 10,000 times gravity for 15 minutes. The cell pack was then separated, weighed, and frozen for storage.

For assay or use, the cell pack or a proportionate part of it was brought back to its original volume with distilled water, and the cells were resuspended. When reconstituted, the cell suspension was assayed in the manner described below.

CONVERSION OF THE CELL SUSPENSION TO SOLUBILIZED FORM

To prepare the enzyme for assay, it is first necessary to convert it to a soluble form. A suitable means for accomplishing this is by sonication.

Cells from a known volume of culture broth are resuspended in 0.05 molar phosphate buffer (pH 7.5). The suspension is then sonified using a Branson Sonifier Model 185-D (20 kc) until the microbial cells of the sample are sufficiently disrupted so that the isomerase enzyme is substantially all liberated. Holding the sample tube in an ice bath during sonication prevents overheating and enzyme inactivation.

The resulting enzyme preparation was a solution of solubilized xylose isomerase.

ASSAY OF ISOMERASE ACTIVITY

The assay procedure involved making a spectrophotometric determination of the ketose produced from a glucose solution under a standardized set of conditions.

A stock solution was made up in the following manner:

Table 4

| Stock Solution for Assay | |
|---|---|
| Component | Amount |
| 0.1 M $MgSO_4 \cdot 7H_2O$ | 1 ml. |
| 0.01 M $CoCl_2 \cdot 6H_2O$ | 1 ml. |
| 1 M Phosphate buffer, pH 7.5 | 0.5 ml. |
| Anhydrous D-glucose | 1.44 g. |
| Distilled water | To make up a total volume of 7.5 ml. |

The enzyme preparation to be assayed was first diluted to contain from 1 to 6 isomerase units per ml.

An enzymatic isomerization was conducted by adding 1 ml. of the enzyme preparation to 3 ml. of the stock solution, and incubating for 30 minutes at 60°C. At the end of the incubation period, a 1 ml. aliquot was taken and quenched in a 9 ml. volume of 0.5 N perchloric acid. The quenched aliquot was then diluted to a total volume of 250 ml. As a control, for comparative purposes, a glucose blank was also run by substituting 1 ml. of water for the 1 ml. of the enzyme preparation in solution form, at the beginning of the incubation period.

The ketose was then determined by a cysteine-sulfuric acid method. For the purposes of this assay, one isomerase unit is defined as the amount of enzyme activity that is required to produce one micromole of levulose per minute under the isomerization conditions described. The assay results are summrized below in Table 5.

Table 5

| Culture | ASSAY RESULTS | | | |
|---|---|---|---|---|
| | Medium A (no Xylose) | | Medium B (Xylose) | |
| | Isomerase Activity | Dry Cell Weight | Isomerase Activity | Dry Cell Weight |
| | μ/ml | g/liter | μ/ml | g/liter |
| Parent strain | 0.24 | 6.45 | 7.46 | 8.75 |
| Parent strain | 0.04 | 6.56 | 6.63 | 9.32 |
| Mutant CPC 3 | 5.48 | 6.87 | 2.73 | 8.81 |
| Mutant CPC 4 | 2.06 | 6.44 | 5.51 | 5.82 |
| Mutant CPC 6 | 3.02 | 5.87 | 3.72 | 5.39 |
| Mutant CPC 7 | 1.45 | 6.66 | 3.00 | 9.58 |
| Mutant CPC 8 | 3.11 | 6.45 | 5.37 | 8.08 |
| Mutant CPC 9 | 1.95 | 6.52 | 3.54 | 6.93 |
| Mutant CPC 10 | 2.14 | 6.72 | 2.70 | 7.17 |
| Mutant CPC 11 | 1.58 | 6.33 | 3.46 | 5.99 |
| Mutant CPC 12 | 2.88 | 7.27 | 5.50 | 8.08 |
| Mutant CPC 13 | 2.05 | 7.33 | 2.16 | 10.27 |
| Mutant CPC 14 | 2.37 | 7.17 | 6.05 | 7.14 |

Mutant strains CPC3, CPC 4, and CPC 8 were selected for continued maintenance. One week after securing the results reported above, each of these three mutants was again used to inoculate the two respective culture media, with the following results.

Table 6

| Culture | SECOND ASSAY RESULTS | | | |
|---|---|---|---|---|
| | Medium A (no Xylose) | | Medium B (Xylose) | |
| | Isomerase Activity | Dry Cell Weight | Isomerase Activity | Dry Cell Weight |
| | μ/ml | g/liter | μ/ml | g/liter |
| Mutant CPC 3 | 4.80 | 5.39 | 11.42 | 7.53 |
| Mutant CPC 4 | 5.70 | 6.44 | 9.68 | 7.30 |
| Mutant CPC 8 | 2.97 | 6.10 | 4.43 | 6.39 |

These observations were considered to establish that the mutants had the capability of producing xylose isomerase without the need for xylose in the culture medium. In addition, it was observed that some of the cultures produced substantially more enzyme than the parent strain, when grown in a culture medium containing xylose. This characteristic is very important for commercial purposes, since greater productivity means that less fermentor capacity is required for a given amount of enzyme production.

EFFECT OF THE CARBOHYDRATE SOURCE IN THE CULTURE MEDIUM

To demonstrate the effect of the source of carbohydrate in the culture medium, and also to demonstrate the ability of mutant strain CPC 3 to produce enzyme when cultured in the presence of a variety of carbohydrates as the sole carbon source, several selected strains of *Streptomyces* were cultured. The culture medium was identical in each case, except for the carbohydrate present. Other conditions were held constant.

The observations made are recorded below in Table 7.

As these observations demonstrate, strains other than mutant strains CPC 3 produced very little enzyme when cultured in all of the culture media employed which did not contain xylose. However, the mutant produced enzyme in more copious quantities in the absence of xylose, and even greater quantities when cultured in the presence of xylose.

Table 7

Effect of Type of Carbohydrate Present on Production of Isomerase with *Streptomyces* Cultures

| Organism | Glycerin 2% | Mannose 2% | Glucose 1.5% | 15 D.E. Starch Hydrolyzate 2% | 15 D.E. Starch Hydrolyzate 1% Xylose 2% |
|---|---|---|---|---|---|
| | Glucose Isomerase Activity, Units/ml | | | | |
| *S. phaeochromogenes* NRRL B2119 | — | — | 0.3 | 0.2 | 1.4 |
| *S. griseoruber* | — | — | 0.3 | 0.2 | 4.5 |
| *S. purpeofuscus* IAM-0073 | — | — | 0.3 | 0.2 | 1.3 |
| *S. olivochromogenes* ATCC 21,114 | 0.4 | 0.4 | 0.2 | 0.2 | 3.4 |
| *S. olivochromogenes* Mutant CPC 3 | 1.3 | 1.9 | 2.2 | 2.3 | 6.3 |

CHARACTERIZATION OF THE MICROORGANISM

To characterize in greater detail the microorganisms that are utilized in the practice of the present invention, the following information is presented. This information is assembled in a form that is similar to that used in describing the *Streptomyces* genus of the *Actinomycetales* in Bergey's "Manual of Determinative Microbiology", 7th Edition.

The first description applies to the parent strain, from which the mutants were derived. The other descriptions apply to two mutant strains, CPC 3 and CPC 15, that are preferred for use in the practice of the present invention. Strain CPC 15 is a single colony isolate of strain CPC 3.

*Streptomyces olivochromogenes* ATCC 21,114(Parent)

Aerial mycelium: Filaments with medium to close spirals. Conidia ellipsoidal to spherical.
Gelatin stab: Good growth. Liquefaction within 10 days.
Agar: Wrinkled, tan to gray growth. Brown to brownish-black soluble pigment produced.
Synthetic agar: White aerial and surface mycelium. No pigment produced.
Starch agar: Abundant growth, yellow in color. Starch hydrolyzed.
Glucose agar: Abundant growth, tan to gray to dark gray in color.
Glucose broth: Thin, brown growth, flaky sediment.
Litmus milk: Dark brown ring; rapid coagulation.
Potato plugs: Abundant, white growth. Soluble brown to black pigment produced.
Nitrites produced from nitrates.
Aerobic.
Grows well at 28°–37°C.

STREPTOMYCES OLIVOCHROMOGENES, Mutant CPC 3

*Aerial mycelium:* Filaments with medium to close spirals. Conidia ellipsoidal to spherical.

Gelatin stab: Poor growth at 30 days; no liquefaction apparent.

Agar: Wrinkled, tan to gray growth. Brown to brownish-black soluble pigment produced.

Synthetic agar: White aerial and surfce mycelium. No pigment produced.

Starch agar: No growth, starch not hydrolyzed.

Glucose agar: Abundant growth, tan to gray to dark gray in color.

Glucose broth: Thin, brown growth flaky sediment.

Litmus milk: Dark brown ring; coagulation at 37° C, poor coagulation at 28°C.

Potato plugs: Abundant white growth. Soluble brown to black pigment produced.

Nitrites produced from nitrates.

Aerobic.

Grows well at 28°–37°C.

STREPTOMYCES OLIVOCHROMOGENES, MUTANT CPC 15

*Aerial mycelium:* Filaments with medium to close spirals. Conidia ellipsoidal to spherical.

Gelatin stab: Poor growth at 30 days, no liquefaction apparent.

Agar: Wrinkled tan to gray growth. Brown to brownish-black soluble pigment produced.

Synthetic agar: White aerial and surface mycelium. No pigment produced.

Starch agar: Abundant growth. Starch hydrolyzed.

Glucose agar: Abundant growth, tan to gray to dark gray in color.

Glucose broth: Thin, brown growth; flaky sediment.

Litmus milk: Dark brown ring; coagulation at 37°C; poor coagulation at 28°C.

Potato plugs: Abundant growth; black soluble pigment produced.

Nitrites produced from nitrates.

Aerobic

Grows well at 28°–37°C.

The following mutant strains have been deposited at the American Type Culture Collection and are beig maintained there pursuant to a contract between that collection and the assignee of this patent application.

Table 8

| Strains Deposited | |
|---|---|
| Mutant Strain No. | Culture Deposit No. |
| CPC 3 | 21,713 |
| CPC 4 | 21,714 |
| CPC 15 | 21,715 |
| The American Type Culture Collection has the following address: American Type Culture Collection 12301 Parklawn Drive Rockville, Maryland 20852 | |

The contract with the Culture Collection provides for permanent availability of the culture to the public, upon issuance of the patent. The assignee of the present application has agreed that, if any of these cultures on deposit should die, or is destroyed, during the effective life of the patent, it will be replaced with a living culture of the same organism.

CHARACTERIZATION OF THE ENZYME

A determination of the Michaelis constants (Km) for reaction on xylose and on dextrose was made.

The purpose was to reveal the relative affinities of the enzyme preparation for these substrates. At present, all isomerases that we have examined that convert dextrose directly to levulose are xylose isomerases. The determination was made utilizing sonic extract of the culture.

It was found that a lower Km was obtained when the enzyme preparation acted on xylose than when it acted on dextrose. This established xylose as the natural substrate of the isomerase, and the enzyme as a true xylose isomerase.

The capacity of the xylose isomerases of the mutants of the present invention to accept dextrose as a substrate is believed to be due to close structural similarities between xylose and dextrose. Since the mutants of the present invention produce the isomerase enzyme either in the presence of xylose or in its absence, the enzyme is constitutive rather than necessarily induced only by the presence of xylose in the culture medium. When the culture medium does contain xylose, the enzyme may be both constitutive and induced.

The following examples re presented to describe the invention further.

EXAMPLE 1

Enzyme Production by Mutant Strain CPC 3

This example describes the production of isomerase in accordance with one preferred mode of practicing the present invention.

Spores from a slant of mutant strain CPC 3 were inoculated into a 500 ml. Erlenmeyer flask containing 100 ml. of a sterile medium composed of the ingredients described below in Table 9.

Table 9

| Inoculum Medium Composition* | |
|---|---|
| Ingredients | Weight % |
| 15 D.E. corn syrup solids | 2.0 |
| Corn steep liquor (55% solids) | 3.6 |
| Magnesium sulfate (MgSO$_4$.7H$_2$O) | 0.05 |
| Distilled water | Balance |

*The medium is an aqueous solution with all weights calculated as a percentage of the total medium, including water.

The pH of the culture medium was adjusted to about 7.1 with sodium hydroxide and sterilized at 121°C for 30 minutes. The flask was inoculated and then incubated for about 60 hours at a temperature of about 28°C. on a reciprocating shaker at 120 cycles per minute.

For the second stage of development, a quantity of about 200 ml. of sterile inoculum medium, having the composition described in Table 9, was prepared in each of several 1000 ml. Hinton modified Erlenmeyer flasks. A 10 ml. portion was then removed from the 500 ml. Erlenmeyer flask and transferred into the Hinton modified Erlenmeyer flask. The inoculated flask was then agitated on a Gump rotary shaker at 224 cycles per minute and incubated at a temperature of about 28°C, for about 48 hours.

In the third step of development, four liters of the inoculum medium described in Table 9 was placed in a 7½ liter bench fermentor and sterilized for 30 minutes at about 121°C. The bench fermentor was inoculated from the one liter shake flask, and sparged with air at 4.0 standard liters per minute. The fermentor was equipped with four baffles and an agitator with two impellers of 3.0 inches diameter each. The agitator was operated at a speed of 500 rpm. The fermentation was conducted at about 28°C. for 48 hours.

Finally, 30 liters of culture medium having the composition described in Table 10, below, was placed in a 40 liter pilot plant fermentor and sterilized for 30 minutes at about 121°C.

Table 10

| Fermentation Medium | |
|---|---|
| Ingredients | Weight % |
| Corn syrup liquor (55% solids) | 3.6 |
| Xylose | 1.0 |
| 15 D.E. corn syrup solids | 2.0 |
| Glycine | 0.1 |
| $NH_4NO_3$ | 0.2 |
| $MgSO_4 \cdot 7H_2O$ | 0.05 |

The pilot plant fermentor was then inoculated from the bench fermentor, and continuously sparged with air at the rate of 24.0 standard liters per minute, under a pressure of 15.0 psig. The pilot plant fermentor was equipped with four baffles and the agitator was equipped with two impellers. Each impeller had a blade diameter size of 4.5 inches. The agitator was operated at a speed of 485 rpm. The fermentation was conducted at about 28°C. for 48 hours.

After completion of the fermentation, the isomerase activity of the product broth was measured and found to be between 10 and 11 units per milliliter.

The enzyme production process was then repeated, but the medium in the 40 liter fermentor was modified to contain starch rather than 15 D.E. corn syrup solids, the starch being present in the same amount as the corn syrup solids it replaced. This medium produced enzyme at a somewhat slower rate, because the organism had to hydrolyze the starch. However, the end results indicated no particular advantage in the use of starch in place of the corn syrup solids, so far as enzyme production was concerned.

EXAMPLE 2

Enzyme Production by Mutant Strain CPC 4

The enzyme production procedures described above, which were used with mutant CPC 3, were repeated using mutant strain CPC 4. Generally comparable enzyme production was obtaied, and there was no indication that the replacement of corn syrup solids by starch in the medium had any effect on enzyme production other than that the medium containing the corn syrup solids did produce enzyme at a greater rate, reaching its peak about 8 hours sooner. In all four fermentations, the culture broth activity fell in the range from about 10 to about 11 units per milliliter.

EXAMPLE 3

Enzyme Production: Variation in the Culture Medium And Other Operating Parameters Several additional fermentations were conducted to produce culture broth having isomerase activity.

In several of these fermentations, the culture medium was modified, generally at the 7½ liter and 40 liter stages. For the purpose of this set of fermentations, a fermentation medium was prepared having the following composition.

Table 11

| Fermentation Medium Composition | |
|---|---|
| Ingredients | Weight % |
| | Medium B |
| Corn steep liquor | 4.0 |
| Xylose | 1.0 |
| Glycine | 0.1 |
| Ammonium nitrate | 0.2 |
| Magnesium sulfate heptahydrate | 0.05 |
| Dextrose | 0.2 |
| Starch | 2.0 |

Variations were made in the fermentation media for different fermentation runs, by the addition of small amounts of such additives as more corn steep liquor, 15 D.E. corn syrup solids, and the like.

All of the fermentations successfully produced culture broth containing a satisfactory level of isomerase activity, during fermentations of the two mutant strains, CPC 3 and CPC 4. Neither strain required the presence of cobalt in the medium to enhance enzyme production, and both strains produced glucose isomerase in much greater quantities than the parent strain. Enzyme activities as high as 15 units per milliliter were obtained, which is substantially higher than the activity generally obtained upon fermentation with the parent strain.

EXAMPLE 4

Enzymatic Isomerization

To demonstrate the effectiveness of the isomerase produced by the mutant strains for converting dextrose to levulose, several conversions were conducted. The enzyme preparation employed consisted of frozen whole cells of either mutant strain CPC 3 or mutant strain CPC 4. There do not appear to be any detectable differences in these enzyme preparations.

A series of conversions of 95 D.E. corn starch hydrolyzate was conducted, using several different enzyme dosages. The conversions were conducted at 70°C., at a pH of 6.25. Magnesium sulfate was added to the hydrolyzate at the level of 0.01 molar. The dry substance level of the hydrolyzate was at about 600 mg./ml. During isomerization, the hydrolyzate was maintained under an atmosphere of nitrogen, and the pH was maintaied by titration as necessary. The hydrolyzate was agitated throughout by stirring with bars in the conversion reactor, driven by a magnetic stirring motor.

The results are reported below in Table 12.

Table 12

| Dosage U/g | Dosage Series Without Cobalt % Conversion of 95 D.E. Hydrolyzate to Ketose Age of Conversion in Hours | | | |
|---|---|---|---|---|
| | 16–18 | 40–44 | 64–66 | 88–90 |
| 0.8 | 17.7 | 30.2 | 35.2 | 38.1 |
| 1.0 | 21.9 | 35.6 | 40.4 | 43.0 |
| 1.2 | 24.7 | 37.5 | 41.3 | 42.0 |
| 1.4 | 26.0 | 40.1 | 43.4 | — |
| 1.6 | 28.1 | 41.0 | 43.2 | — |
| 2.0 | 33.4 | 43.2 | 45.2 | — |

As these data demonstrate, an enzyme dosage of 1.0 units per gram is adequate to produce enough levulose to provide a 40% ketose level after a 66 hour conversion without cobalt; and an enzyme dosge of 1.4 units per gram is adequate for the production of 40% ketose after 42 hours of conversion time.

Several additional conversions were conducted successfully at 65°C. In addition, some of the conversions were conducted successfully at somewhat higher pH values. The results observed are summarized below.

Table 13

Conversion at 65°C Without Cobalt
% of 95 D.E. Hydrolyzate Converted to Ketose

| pH | Dosage U/g | Age of Conversion in Hours | | | |
|---|---|---|---|---|---|
| | | 22 | 43 | 69 | 88 |
| 6.25 | 0.7 | 16.5 | 24.1 | 30.0 | 36.9 |
| 6.25 | 1.0 | 20.3 | 30.0 | 36.6 | 42.1 |
| 6.50 | 0.7 | 16.9 | 25.9 | 31.9 | 36.3 |
| 6.50 | 1.0 | 23.4 | 33.3 | 38.8 | 42.6 |
| 6.75 | 0.7 | 18.9 | 28.2 | 33.6 | 37.2 |
| 6.75 | 1.0 | 22.1 | 30.1 | 36.0 | 39.5 |

The results observed appear to demonstrate that the use of the higher conversion temperature of 70°C. is somewhat preferable. The higher pH levels did not appear to produce any advantage.

To summarize, it would appear that conversions conducted at 70°C., at a pH of about 6.25, and at a dry substance level in the range from about 600 mg./ml. to about 800 mg./ml., with an enzyme dosage of about 1.2–1.4 units per gram, for from 40 to 48 hours approximately, and in the presence of about 0.01 molar magnesium, in the absence of cobalt and with nitrogen sparging, will produce highly satisfactory sweet syrup products. Compositions of the following kind can be expected:

Table 14

Sweet Syrup Compositions

| Ingredient | Weight %, Dry Substance Basis |
|---|---|
| Levulose | 40 – 44 |
| Dextrose | 45 – 50 |
| Higher Saccharides | 7 – 8 |

These data demonstrate that a 40% levulose syrup can be made economically from a 95 D.E. hydrolyzate utilizing enzyme preparations derived from the mutants of the present invention, without the use of added cobalt.

CONCLUSION

Although the taxonomy of several strains of the mutant microorganisms of the present invention has been reported above, with some attention to morphology, it will be obvious to those skilled in the art that the production of a physiological mutant may be accompanied by morphological changes, but that the variation in biochemical activity is not related to a specific morphological change. It will also be obvious that a particular mutant may be isolated from natural sources as well as from survivors of exposure to artificial mutagenic agents.

Moreover, it will also be obvious that within the *Streptomyces* genus, the same type of mutant can be obtained from different species of xylose isomerase producers, and that the type of mutant produced upon exposure to mutagenic agents is not dependent on the type of mutagenic agent used.

Therefore, although descriptions of the taxonomy of one parent strain and of two mutant strains, derived from the parent with ultraviolet irradiation, have been reported in detail above, the description of the mutants do not necessarily characterize all strains, variants, or sub-mutants of the new mutants, nor do they necessarily distinguish the new mutant forms from other strains of *Streptomyces olivochromogenes*.

Mutant strains of microorganisms that can be employed in the practice of the present invention can, in general, be readily identified by application of the following criteria:

1. Taxonomy that is characteristic of the *Streptomyces* genus.
2. Production under identical conditions of cultivation, particularly under those conditions described herein, of at least 50% more xylose isomerase activity than *Streptomyces olivochromogenes* 21,114, and preferably, twice as much.
3. Production of appreciable quantities of xylose isomerase when cultivated in nutrient media free of xylose and xylose-supplying materials.
4. Preferably, in addition, production of appreciable quantities of xylose isomerase when cultivated in nutrient media free of added cobalt.

The particularly preferred mutant strains are those of *S. olivochromogenes*.

The terms, "a *Streptomyces* mutant", and, "a mutant strain of *S. olivochromogenes*", and the like, as used in this application are intended to include those cultures of microorganisms of the *Streptomyces* genus that are identifiable by the above criteria. These terms therefore include naturally occurring variants and artificially induced variants of strains that are specifically characterized herein and that are also identifiable by the above criteria.

The enzyme preparaion that is produced from the mutant strains of microorganisms that can be used in practicing the present invention may take substantially any desired form. Good isomerization results have been observed when alcohol dehydrated cells were employed for effecting the conversion, at a dosage of about 1.3 units of activity per gram of dry substance. For example, when a 30° Be corn starch hydrolyzate at 95 D.E. was converted at an enzyme dosage of 1.3 units of activity per gram of dry substance at 70°C. (158°F.), utilizing alcohol dehydrated cells, at pH 6.25, for 46 hours, a levulose content of 40% was achieved in 37 hours and the final levulose content of the product was about 41%. The sweet syrup product filtered easily and refined well.

Other forms of enzyme preparation can also be used effectively. One preferred form of enzyme preparation is the culture broth that is removed from a fermentor on a continuous basis during a continuous fermentatin, since this represents a very economical production technique.

Enzyme preparations obtained in accordance with the present invention generally will be used to isomerize dextrose at a pH in the range from about 6 to about 7, and at a temperature in the range from about 60°C. to about 70°C. However, they are operative to effect isomerization outside of these ranges.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the appended claims.

What is claimed is:

1. A process for producing a xylose (dextrose) isomerase enzyme preparation which comprises:
   a. culturing cells derived from a mutant strain of a microorganism of the Streptomyces genus in a nutrient medium, said mutant strain being characterized in that when cultivated in a nutrient medium that is free of xylose and xylose-supplying materials, it produces at least 50% more xylose (dextrose) isomerase activity than Streptomyces olivochromogenes ATCC No. 21,114 under identical conditions of cultivation, and
   b. obtaiing a xylose (dextrose) isomerase enzyme preparation that is capable of enzymatically isomerizing dextrose to levulose in the absence of added cobalt.

2. The process of claim 1, wherein said mutant strain is characterized in that when cultivated in a nutrient medium that is free of xylose and xylose-supplying materials, it produces twice as much xylose (dextrose) isomerase activity than Streptomyces olivochromogenes ATCC No. 21,114 under identical conditions of cultivation.

3. The process of claim 1, wherein the nutrient medium contains xylose or a xylose-supplying material.

4. The process of claim 1, wherein the nutrient medium is free of added cobalt and the xylose (dextrose) isomerase obtained possesses a xylose isomerase activity as high as 15 isomerase units per millileter.

5. The process of claim 1, wherein the nutrient medium contains corn steep liquor, xylose, glycine, ammonium nitrate, magnesium sulfate heptahydrate, dextrose and starch.

6. The process of claim 1, wherein the microorganism is a mutant of Streptomyces olivochromogenes.

7. The process of claim 1, wherein the mutant strain is a member selected from the group consisting of Streptomyces olivochromogenes ATCC No. 21,713, Streptomyces olivochromogenes ATCC No. 21,714, Streptomyces olivochromogenes ATCC No. 21,715, variants and sub-mutants of said mutant strains.

8. A process for the production of a xylose (dextrose) isomerase enzyme preparation, which comprises:
   a. inoculating a nutrient medium that is free from xylose and xylose-supplying material with cells derived from a mutant strain of a microorganism of the Streptomyces genus, said mutant strain being characterized in that when cultivated in a nutrient medium that is free of xylose and xylose-supplying materials, it produces twice as much xylose (dextrose) isomerase activity than Streptomyces olivochromogenes ATCC No. 21,114 under identical conditions of cultivation to produce cells containing xylose (dextrose) isomerase,
   b. fermenting the cells in said nutrient medium from (a) wherein at least the final stage of fermentation, the nutrient medium contains xylose; and
   c. recovering the xylose (dextrose) isomerase enzyme produced.

9. The process of claim 8, wherein the nutrient medium in (a) and (b) are free from added cobalt.

10. The process of claim 8, wherein the nutrient medium in (b) contains corn steep liquor, xylose, glycine, ammonium nitrate, magnesium sulfate heptahydrate, dextrose and starch.

11. The process of claim 8, wherein the nutrient strain is a member selected from the group consisting of Streptomyces olivochromogenes ATCC No. 21,713, Streptomyces olivochromogenes ATCC No. 21,714, Streptomyces olivochromogenes ATCC No. 21,715, variants and sub-mutants of said mutant strains.

12. A process for the production of a xylose (dextrose) isomerase enzyme preparation, which comprises:
   a. inoculating a nutrient medium that is free from added cobalt with cells derived from a mutant strain of a microorganism of the Streptomyces genus, said mutant strain being a member selected from the group consisting of Streptomyces olivochromogenes ATCC No. 21,713, Streptomyces olivochromogenes ATCC No. 21,714, Streptomyces olivochromogenes ATCC No. 21,715, variants and sub-mutants of said mutant strains to produce cells containing xylose (dextrose) isomerse;
   b. fermenting the cells in said nutrient medium from (a), wherein at least the final stage of fermentation, the nutrient medium contains xylose; and
   c. recovering the xylose (dextrose) isomerase produced.

13. The process of claim 12, wherein the nutrient medium of (a) is free from xylose and xylose-supplying material and the nutrient medium in (b) contains corn steep liquor, xylose, glycine, ammmonium nitrate, magnesium sulfate heptahydrate, dextrose and starch.

14. A process for the production of a xylose (dextrose) isomerase enzyme preparation which comprises:
   a. inoculating a nutrient medium that is free from xylose and xylose-supplying materials and free from added cobalt with cells derived from the mutant strain Streptomyces olivochromogenes ATCC No. 21,715, which is a single colony isolate of the mutant strain Streptomyces olivochromogenes ATCC No. 21,713 to produce cells containing xylose (dextrose) isomerase;
   b. fermenting the cells in said nutrient medium from (a), wherein at least the final stage of fermentation, the nutrient medium contains xylose; and
   c. recovering the xylose (dextrose) isomerase produced.

15. The process of claim 14, wherein the nutrient medium of (b) contains corn steep liquor, xylose, glycine, ammonium nitrate, magnesium sulfate heptahydrate, dextrose and starch.

* * * * *